United States Patent [19]

Moore et al.

[11] Patent Number: 4,633,881

[45] Date of Patent: Jan. 6, 1987

[54] AMBULATORY VENTRICULAR FUNCTION MONITOR

[75] Inventors: Richard H. Moore, Concord; H. William Strauss, Newton Centre; Nathaniel M. Alpert, Swampscott, all of Mass.

[73] Assignee: The General Hospital Corporation, Boston, Mass.

[21] Appl. No.: 394,465

[22] Filed: Jul. 1, 1982

[51] Int. Cl.$^4$ .................................................. A61B 6/00
[52] U.S. Cl. ...................................... 128/659; 128/710
[58] Field of Search ............... 128/653, 654, 659, 644, 128/708

[56] References Cited

U.S. PATENT DOCUMENTS

| | | | |
|---|---|---|---|
| 3,215,136 | 11/1955 | Holter et al. | 128/712 |
| 3,409,007 | 11/1968 | Fuller | 128/644 |
| 3,525,330 | 8/1970 | Greene | 128/644 |
| 3,769,966 | 11/1973 | Youdin et al. | 128/654 |
| 3,949,210 | 4/1976 | Eichinger | 250/370 |
| 4,033,335 | 7/1977 | Nickles | 128/659 |
| 4,047,037 | 9/1977 | Schlosser et al. | 250/370 |
| 4,121,575 | 10/1978 | Mills et al. | 128/644 |
| 4,123,785 | 10/1978 | Cherry et al. | 128/712 |
| 4,245,646 | 1/1981 | Ionnou et al. | 128/653 |

FOREIGN PATENT DOCUMENTS 2704256  3/1978  Fed. Rep. of Germany .

OTHER PUBLICATIONS

Abstracts "Circulation", vols. 59–60, supp. II, Oct. 1979, p. II-246.

Primary Examiner—William E. Kamm
Attorney, Agent, or Firm—Weingarten, Schurgin, Gagnebin & Hayes

[57] ABSTRACT

An ambulatory ventricular function anaylzer system is provided. The ambulatory ventricular function analyzer system is carried by a garment worn by a cardiac patient and includes ECG electrodes, a main left ventricular probe detector, and a background lung probe detector for providing diagnostically useful information while the patient goes about the normal activities of daily life. An information processing sub-system including a microprocessor responds to the electrode signal and to the probe signals and provides composite data representative of the ECG activity, the background lung time-activity, the left ventricular time-activity, and an R-wave histogram averaged over multiple cardiac cycles. The averaged data is sequentially sotred over a long time interval on magnetic tape in plural categories representing premature ventricular contraction, post-premature ventricular contraction, and normal ventricular contraction for subsequent display on a computer-based graphics display for study by a cardiac specialist. The main left ventricular function probe detector includes an array of cadmium telluride crystals mounted in a Pb housing having a parallel hole Pb collimator. The detector is substantially insensitive to position changes that arise during ambulatory monitoring.

28 Claims, 16 Drawing Figures

FIG. 7A NORMAL INTERVAL
STORAGE REGISTER
| 64 REGISTERS FOR ECG |
| 64 REGISTERS FOR MAIN DET |
| 64 REGISTERS FOR BACKGROUND |
FIG. 7B SHORT INTERVAL
| 64 ECG |
| 64 MAIN DETECTOR |
| 64 BACKGROUND DET |
FIG. 7C LONG INTERVAL
| 64 ECG |
| 64 MAIN DETECTOR |
| 64 BACKGROUND DET. |
FIG. 7D
| R-WAVE HISTOGRAM REGISTER FOR EACH R-R INTERVAL |
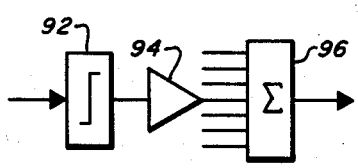
*FIG. 4A*
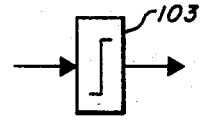
*FIG. 4B*

ECG
(SMOOTHED)

MAIN DET
(BLOOD VOLUME)

BACKGROUND

R-WAVE HISTOGRAM
NO BEATS

FREQ. BEATS

AMBULATORY VENTRICULAR FUNCTION MONITOR

The invention described herein was made in the course of work under Grant No. HL 246623 from the Department of Health and Human Services.

FIELD OF THE INVENTION

This invention is drawn to the field of cardiology, and more particularly, to a novel ambulatory ventricular function monitor.

BACKGROUND OF THE INVENTION

Several radiopharmacological techniques are known to monitor ventricular cardiac performance. Contrast angiography, radionuclide tracer injection using scintillation counters, and nuclear gated blood pool scanning are representative of the clinically-approved medical procedures.

The diagnostic usefulness of the known medical procedures is limited by the narrow range of patient activities permitted when the tests are administered. Typically, the ventricular activity of the heart is monitored only in a basal state or under a carefully controlled stress condition during clinical or laboratory patient testing. The heart dysfunction which may be precipitated in the performance of the activities of daily living, as well as the relative duration of certain degrees of such dysfunction, are thereby lost to the cardiologist with an attendant disadvantage to modern diagnosis, therapy planning, and cardiac patient health.

SUMMARY OF THE INVENTION

The novel ambulatory ventricular function analyzer system of the present invention is capable of recording cardiac conditions under circumstances that are incapable of creation in the laboratory or in the clinic thereby providing improved diagnosis and therapy planning capability. The instrument system of the invention is of such weight and dimensions as to be carried in a garment worn about the body of a cardiac patient and is operative to continuously and concurrently record, over an extended period, both the ventricular heart function, monitored from detection of radiation-emitting sites in the blood, and the electrocardiographic (ECG) activity while the patient is engaged in the normal performance of the activities of daily life. The instrument system of the invention preferably uses two CdTe radionuclide detectors for monitoring ventricular function and two leads for continuous ECG monitoring.

Each ECG cycle is analyzed to detect variations in heart rate defined by a premature ventricular contraction (PVC), a normal ventricular contraction (NVC), and a post-premature ventricular contraction (PPVC). Data representing ventricular and ECG signals respectively obtained during PVC, NVC, and PPVC are separately accumulated over many cardiac cycles and stored. The data is displayed on a computer-based graphics terminal in a number of modes including time sequential for displaying the correlation of specific cardiac dysfunction data with time and ECG activity, and in a time-compressed overlapped mode for displaying large intervals of stored data in a manner where the point of cardiac dysfunction can readily be identified.

The ambulatory ventricular function monitor includes a small (lightweight) and rugged nuclear probe detector assembly for sensing ventricular heart function. The assembly has a planar array of CdTe radiation-sensitive crystals and a parallel hole, lead collimator in a lead housing. A threshold, summer, and discriminator circuit is responsive to the output signals of the CdTe crystal detectors and operative to sum those signals that exceed a predetermined threshold. The detector prevents likely position-shifting of the detectors from influencing the system data and compensates for motion of the heart away from the detector.

Accordingly, it is an object of the present invention to provide an ambulatory ventricular function monitor to reliably monitor ventricular performance continuously over an extended time period.

Another object is to provide such a monitor that can be easily worn in a garment.

Another object is to provide such a monitor that displays the degree of, type of, and time of occurrence of ventricular dysfunction.

Another object is to provide such a monitor that provides composite data that represents continuous averages of sensor data over short time intervals.

Another object is to provide such a monitor that displays right or left lung time-activity.

Yet another object is to provide such a monitor that provides such composite data in plural categories representing premature ventricular contraction, normal ventricular contraction, and post-premature ventricular contraction over long time intervals.

Other objects, advantages, and features will become apparent by reference to the following exemplary and non-limiting detailed description of the invention, and to the drawings, wherein:

BRIEF DESCRIPTION OF THE DRAWINGS

FIGS. 4A and 4B illustrate threshold comparator circuits for use in the system of FIG. 4.

FIGS. 7A, B, C, and D show a diagram of the information storage system of the ventricular function monitor of the invention.

DESCRIPTION OF THE PREFERRED EMBODIMENT

Figure 1:
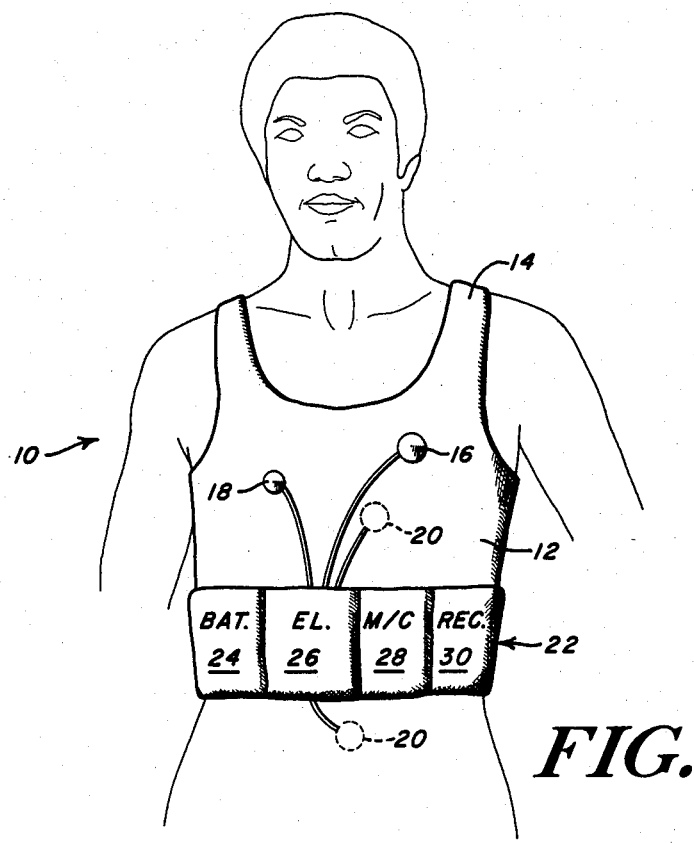
FIG. 1 is a stylized pictorial view of an ambulatory ventricular function monitor system of the invention.

Referring now to FIG. 1, generally shown at 10 is a stylized pictorial view of a novel ambulatory ventricular function monitor system according to the present invention. The system 10 includes a garment 12 having shoulder straps 14, main and background nuclear probes 16 and 18, respectively, ECG electrodes 20, and an instrument system generally designated at 22 carried by the garment 12 and connected to the nuclear probes 16 and 18 and to the electrodes 20.

The main detector 16 to be described is preferably positioned over the left ventricle of the heart. The background detector 18 is preferably positioned over the right lung but may be positioned over the left lung as well. Probes 16 and 18 are responsive to the presence of a suitable radiopharmaceutical injected into the circulatory system and provide output signals to the instrument system 22 that are proportional to the level of radiation emitted by the radiopharmaceutical over the cardiac cycle. The signal produced by the main nuclear detector 16 is representative of the left ventricular time-activity of the heart and the signal produced by the background detector 18 is representative of the left or right lung time-activity.

Electrodes 20, shown in dashed lines, are positioned in well-known locations to monitor and detect the circulating currents produced by the ECG activity of the heart. The output signals produced by the electrodes 20 are representative of the ECG activity of the heart from cycle-to-cycle and are provided to the instrument system 22. Preferably, two bipolar precordial leads are used and monitored simultaneously. The exploring electrodes are positioned at the xiphoid process and fifth rib at the anterior auxiliary line.

The instrument system 22 is composed of a power module 24 (BAT), an electronics module 26 (EL), an information processing module 28 (M/C), and an informatiion storage module 30 (REC). The modules 24, 26, 28, and 30 are carried by the garment 12 by any suitable means such as in respective pockets dimensioned to securely support the corresponding modules. Other suitable means for supporting the ambulatory ventricular function monitor of the invention such as a knapsack, multiple garments, a tethered arrangement and the like are contemplated. The module 24 preferably includes longlife batteries and an AC adaptor for use in critical patient care.

The instrument system 22 preferably includes a microcomputer, M/C, responsive to the ECG and nuclear probe output signals and operative to provide highly reliable data representing the nuclear ventricular time-activity, the nuclear lung time-activity, and the ECG activity of the heart averaged over many cardiac cycles which is stored on magnetic recording tape, REC, in respective categories depending upon whether the interbeat interval of the cardiac cycle is short, long, or normal. The data may be displayed later in the lab or office for study by a cardiac specialist so that the type, degree, and time of dysfunction may be ascertained.

Figure 2:
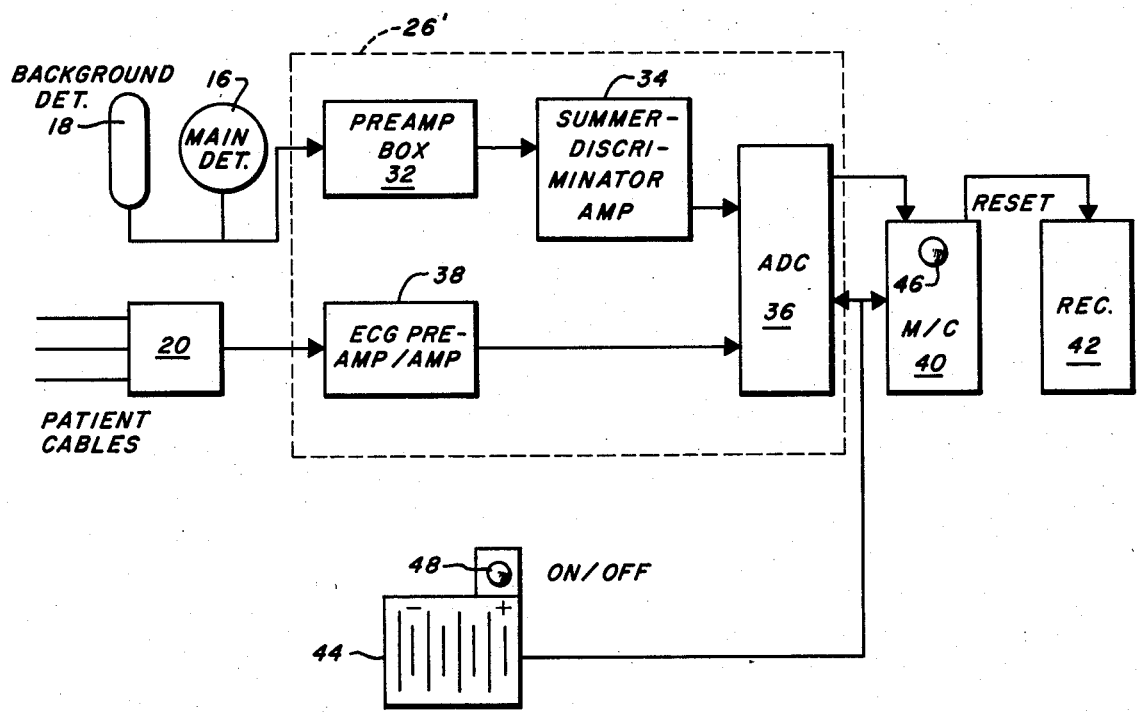
FIG. 2 is a block diagram of an instrument of the ambulatory ventricular function monitor of the invention.

Referring now to FIG. 2, which shows a block diagram of the instrument system 22 of the ambulatory ventricular function monitor of the invention, the main 16 and the background 18 nuclear probe detector output signals are connected through a preamplifier module 32 to a summer discriminator amplifier (SDA) module 34. The output of the SDA 34 is connected to an analog-to-digital converter (ADC) module 36. The output signal produced by the ECG electrodes 20 are connected to the analog-to-digital converter module 36 through a preamplifier/amplifier module 38. An information processing module 40, preferably a 6800-type microcomputer although any suitable microcomputer or hardwired arrangement of logic elements may be employed, is connected to the output of the analog-to-digital converter module 36. An information storage module 42, preferably a suitable magnetic tape recorder, is connected to the data output terminals of the microcomputer 40. Bubble memory devices, tiny discs, and other information storage media may be utilized as well. A battery or other power source 44 is connected to the analog-to-digital converter module 36 and to the microcomputer module 40. A switch 46 is provided on the microcomputer 40 which is operative to initialize and reset all registers of the information processing module of the invention to be described, and a switch 48 is provided on the battery 44 to turn the system either on or off. As shown by the dashed box 26', the electronics module 26 of FIG. 1 may advantageously be composed of the nuclear probe preamplifier module 32, the ECG preamplifier module 38, the SDA module 34, and the ADC module 36.

Figure 3:
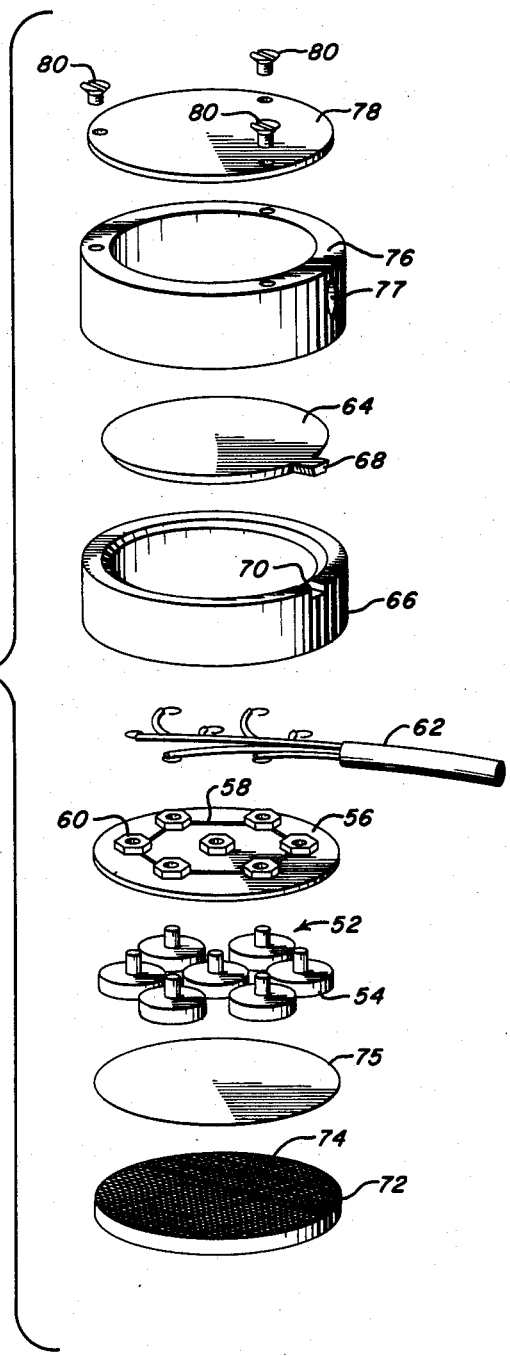
FIG. 3 is an exploded perspective view of a small (lightweight) and rugged probe detector assembly of the ventricular function monitor of the invention.

Referring now to FIG. 3, generally designated at 50 is an exploded perspective view of a small, lightweight, and rugged nuclear probe detector assembly of the ambulatory ventricular function monitor of the invention. The assembly weighs about four pounds. The nuclear probe detector assembly 50 includes an array 52 of gamma photon radiation-sensitive crystals 54. Preferably seven cadmium telluride, CdTe, crystals are arrayed in a plane to provide a mosaic detector. Other suitable gamma photon radiation sensors such as one or more sodium iodide crystals with an avalanche photodiode readout, plastic scintillation detectors with an avalanche photodiode readout, high sensitivity germanium crystals, mercury cadmium telluride crystals and bismuth germanate crystals with an avalanche photodiode readout may also be employed.

The crystals 54 of the array 52 are mounted to a printed circuit board 56. Board 56 is provided with an etched metalization common ground pattern 58 and a plurality of insulative electrode support pads 60. A coaxial cable 62, having a plurality of leads corresponding in number to the number of the crystals 54, is preferably used for electrical connection to the ungrounded leads of respective ones of the crystals 54.

The detector array 52 is mounted in a foamed plastic support, not shown, in a two-piece lead radiation shield having a cover plate 64 adapted to flush mount the rim of a cylindrical housing 66. A laterally and outwardly projecting rib 68 is formed on the cover 64 which is adapted to abut a recess 70 formed in the rim of the cylindrical housing 66 to provide ease of disassembly of the shield.

A lead collimator 72 is mounted over the array 52 to the mouth of the lead shield. The collimator 72 is provided with a plurality of parallel holes 74 therethrough. A copper ground shield 75 is mounted between and abutting the array 52 and the collimator 72 in the lead shield.

The shielded mosaic nuclear probe detector assembly is mounted in an aluminum housing composed of a cylindrical aluminum can 76 and an aluminum cover plate 78. The cover plate 78 is fastened to the rim of the cylindrical can 76 preferably by threaded fasteners 80. The side wall of the can 76 is provided with an aperture 77 through which the coaxial cable 62 extends.

The combination of the parallel hole lead collimator 72 and mosaic detector array 52 cooperate to provide a nuclear probe output signal that is substantially insensitive to the slight positional changes in probe position which typically occur in ambulatory use. It has also been found that the detector array avoids the amplification of the signal caused by the motion of the ventricle away from the detector. The background detector of the ambulatory ventricular function monitor of the invention is the same as the mosaic detector described above except that a few number of individual CdTe gamma photon radiation-sensitive crystals are used. Two such crystals may advantageously be employed.

Figure 4:
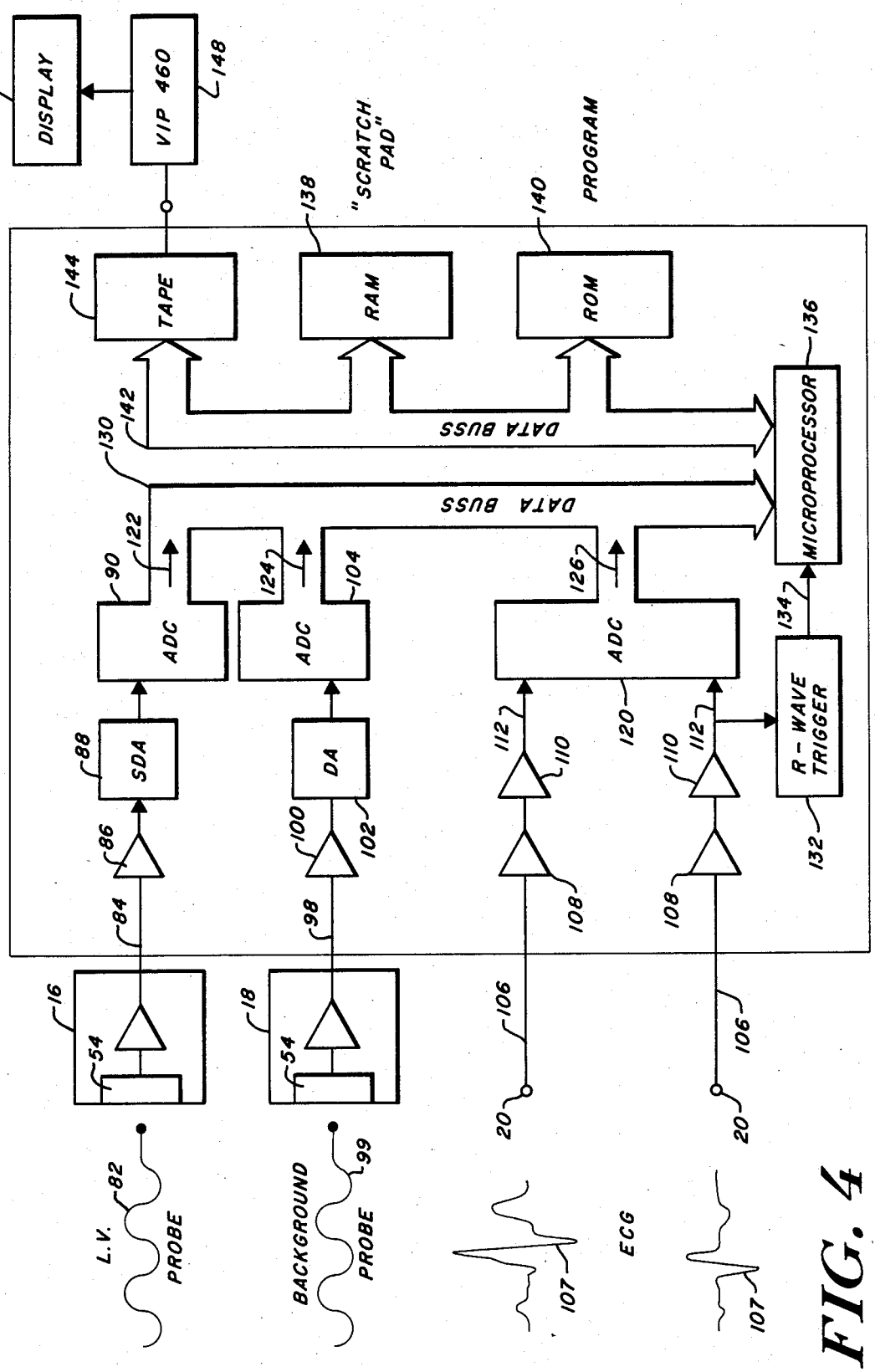
FIG. 4 is a detailed block diagram of the electronics system of the ambulatory ventricular function monitor of the invention.

Referring now to FIG. 4, which shows a detailed block diagram of the electronics and information processing system of the ambulatory ventricular function monitor of the invention, the crystals 54, one of which is shown, of the main left ventricular nuclear probe detector 16 are responsive to the gamma photon radiation 82 emitted by the injected radiopharmaceutical and provide on electrical signal over leads 84 representative of the nuclear ventricular activity of the heart. The signal is amplified in preamplifier 86 and fed through a summer discriminator amplifier (SDA) 88 to an analog-to-digital converter 90. The SDA 88 includes for each lead of the mosaic CdTe crystal detector array of FIG. 3 a threshold comparator 92 and an amplifier 94 as shown in FIG. 4A. Those output signals that exceed the threshold are amplified, and then summed in a summer 96 to provide a measure of noise discrimination.

Figure 5A:
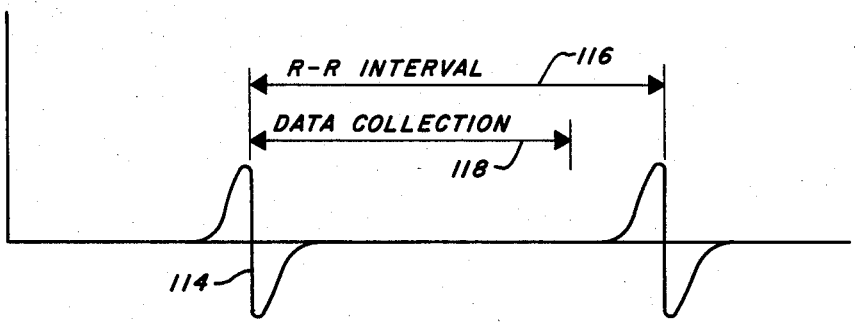
FIG. 5A shows a graph depicting a smoothed ECG signal, FIG. 5B a graph depicting left ventricular detected activity, FIG. 5C, a graph depicting lung activity, and FIG. 5D, a graph depicting an R-wave histogram.
Figure 5B:

The analog output signal of the SDA 88 is shown as a curve 97 in FIG. 5B which represents the left ventricular nuclear time-activity of the heart. The peaks of the curve 97 correspond to times of heat expansion at end diastole and the valleys correspond to times of heat contraction at end systole. When expanded, the level of detected radiation emitted by the radiopharmaceutical is greater since comparatively more blood is present in the expanded volume of the heart. The detected level of emitted radiation is less in the contracted state since comparatively less blood is present in the contracted volume of the heart.

Figure 5C:

In a similar fashion, one or more radiation-sensitive CdTe crystals 54 of the background detector 18 of the types used in the main detector 16, are responsive to the gamma photon radiation 99 emitted by the radiopharmaceutical in the region of the left or right lung and provide an analog signal 98, the amplitude of which is representative of the level of the emitted radiation. This signal is amplified in preamplifier 100 and passed through a discrimination amplifier (DA) 102 having a threshold comparator 103 operative to pass only those signals whose magnitude exceeds the threshold as shown in FIG. 4B. An analog-to-digital converter 104 is connected to the output of the DA 102. Curve 105 of FIG. 5C shows the analog output signal representing the nuclear lung time-activity monitored by the background nuclear detector 18 of the ambulatory ventricular function monitor of the invention.

Electrodes 20 are operative to produce electrical signals over leads 106 that correspond to the ECG activity 107 of the heart. The ECG signal is amplified in preamplifiers 108 and conditioned by low-pass amplifier 110 to produce, in a well-known manner, a smoothed ECG signal having well-known Q, R, and S segments as shown by the curve 114 in FIG. 5A. FIG. 5A also depicts an R—R interval designated at 116 and a data collection interval designated at 118 to be discussed. An analog-to-digital converter 120 is connected to the smoothed ECG signal.

The analog-to-digital converters 90, 104, and 120 are responsive to the analog signal representing the nuclear time-activity of the left ventricle, to the analog signal representing the nuclear time-activity of the right lung, and to the smoothed analog ECG signal and are operative to provide first, second, and third digital pulse streams 122, 124, and 126 the frequency of each of which depends on the amplitude of the corresponding analog signal. The amplitude to frequency modulated digital pulse streams 122, 124, and 126 are coupled via a data bus 130 to a microprocessor 136.

An R-wave trigger circuit 132 of conventional design is responsive to the smoothed analog ECG signal and operative to provide a fourth digital pulse stream over a line 134 to the microprocessor 136. The interpulse interval of the fourth digital pulse stream corresponds to the time separation between the detected peaks on R-segments of the smoothed ECG signal from cycle to cycle as shown by the R—R interval 116 in FIG. 5A. As will appear below, the R-wave pulse stream over the line 134 is used as a trigger for initiating system timing.

Figure 5D:
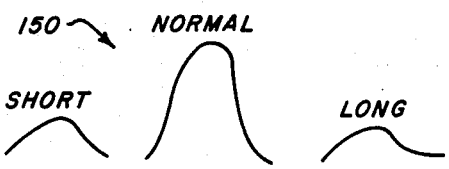

The microprocessor 136 has associated therewith in a conventional manner scratch pad RAM registers 138 and a program ROM 140. As will appear more fully below, the microprocessor 136 is responsive to the first, second, and third digital pulse streams 122, 124, and 126, respectively, and to the R-wave trigger pulse stream over line 134 and operative to provide data over a bus 142 that represents the nuclear ventricular time-activity, the nuclear lung time-activity, and the ECG activity of the heart in plural categories representing normally contracted, premature, and post-premature ventricular beats. The data is stored on an information storage media 144, preferably a magnetic tape, preferably in segments averaged over two and sixteen minute intervals for subsequent analysis on a computer-based graphics display 146 connectable to the recorded tape via a tape reader 148. The processor is also responsive to the third and fourth digital pulse streams and operative to store on the tape recorder 144 an R-wave histogram depicted as a curve 150 in FIG. 5D. The R-wave histogram preferably is produced over each two minute interval for the duration of data collection. Many hours of data are accumulated on the tape while the patient undergoes the activity of ordinary life. The device is ordinarily used in an ambulatory mode but, it should be noted, may also be used for critical patient care.

Figure 6:
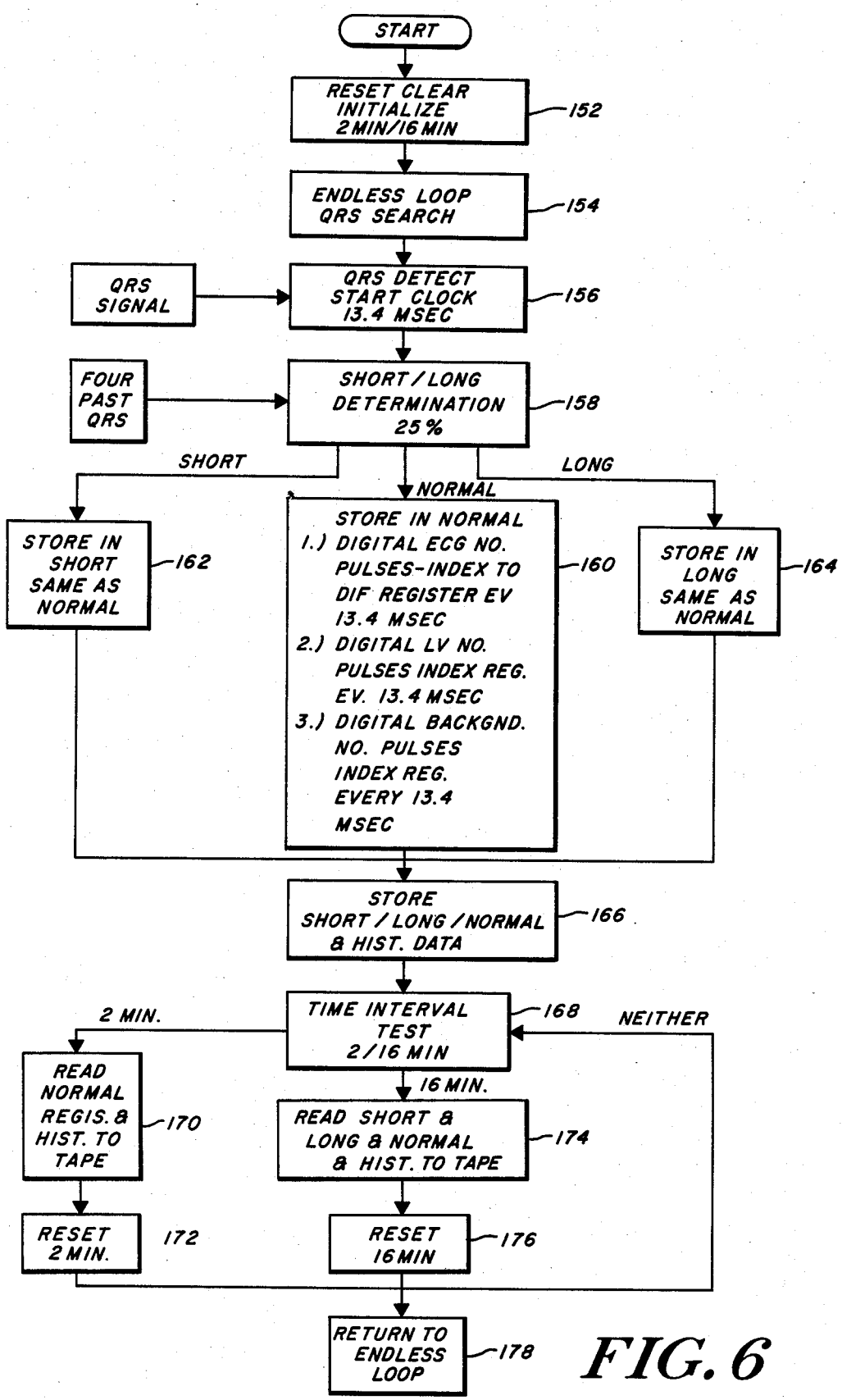
FIG. 6 is a flow chart of the data processing system of the ventricular function monitor of the invention.

The microprocessor 136 is operative according to the flow chart shown in FIG. 6. System operation is commenced by depressing the reset button 46 shown in FIG. 2 which clears and initializes the registers of the RAM 138 of FIG. 4 and preferably starts an internal two minute and sixteen minute clock as shown by the block 152.

An endless loop search is then begun to detect the QRS signal to identify a beat as shown in block 154.

As shown in block 156, upon detection of an R-wave trigger pulse, the processor is operative to activate an internal sampling clock preferably having a 13.4 millisecond period. The processor is then operative to gate the number of pulses which appear in the first, second, and third digital pulse streams during the 13.4 millisecond sampling interval to counting registers shown in FIG. 7. The respective counts are proportional to the amplitude of the corresponding analog signals which represent the nuclear ventricular time-activity, nuclear lung time-activity, and ECG activity of the heart during successive sampling intervals.

As shown in block 158, preferably the prior four R—R intervals are averaged to provide a window parameter representing a normal beat-to-beat interval. The processor is operative to classify the particular R—R interval being processed as normal if it falls within plus or minus a specified fraction, preferably twenty five percent, of the window parameter.

As shown in block 160 for the normal case, the number of pulses which appear in the first, second, and third pulse streams during successive ones of the 13.4 millisecond sampling intervals are indexed for the duration of the data collection interval 118 of FIG. 5A to successive ones of corresponding counting registers dedicated to the left ventricular time-activity, the background nuclear time-activity, and the ECG activity as shown in FIG. 7A. Preferably, the data collection interval is about eight hundred fifty eight milliseconds long, which corresponds to sixty four sampling intervals of the preferred 13.4 millisecond duration. The address of the storage location is determined by the phase of the smoothed ECG pulse stream for each successive 13.4 millisecond sampling interval.

As shown by block 162, if the R—R wave interval is shorter than the normal interval, the counts are accumulated in a similar fashion in separate registers dedicated for premature ventricular contraction interbeat intervals as shown in FIG. 7B.

As shown in block 164, data representing a post-premature ventricular interbeat interval is, in a like manner, separately stored in dedicated long registers as shown in FIG. 7C.

As shown in block 166, during each sampling interval of each data collection window the processor is operative to add the number of pulses present to the count total in the appropriate registers. The count accumulated at each address of the registers shown in FIG. 7 represent, at successive times an average accumulated over the elapsed time interval. In step 166 the R-segment interval as represented by the fourth digital pulse stream produced by the triggering circuit 132 is stored in a register of FIG. 7D.

As shown in block 168, the processor is operative to accumulate counts in the plural categories preferably over a two and a sixteen minute averaging time. Data accumulated during the two minute interval typically correspond to an average over from one hundred twenty to one hundred fifty beats. Data collected during the sixteen minute interval typically correspond to an average over from four hundred eighty to six hundred beats.

As shown in block 170, after the elapse of the two minute averaging interval, the processor is operative to read the data counts accumulated in the normal registers and the histogram registers out to tape, and to reset the two minute clock as shown in block 172.

As shown in block 174, after the lapse of the sixteen minute averaging interval, the processor is operative to read the data counts accumulated in the short (PVC), in the long (PPVC), in the normal (NVC), and in the histogram registers out to tape, and to reset the sixteen minute clock as shown in block 176.

As shown in block 178, the processor is operative to clear the appropriate registers after the elaspe of the successive two and sixteen averaging intervals and return to endless loop search for the duration of data collection which typically is six or more hours.

Figure 8:
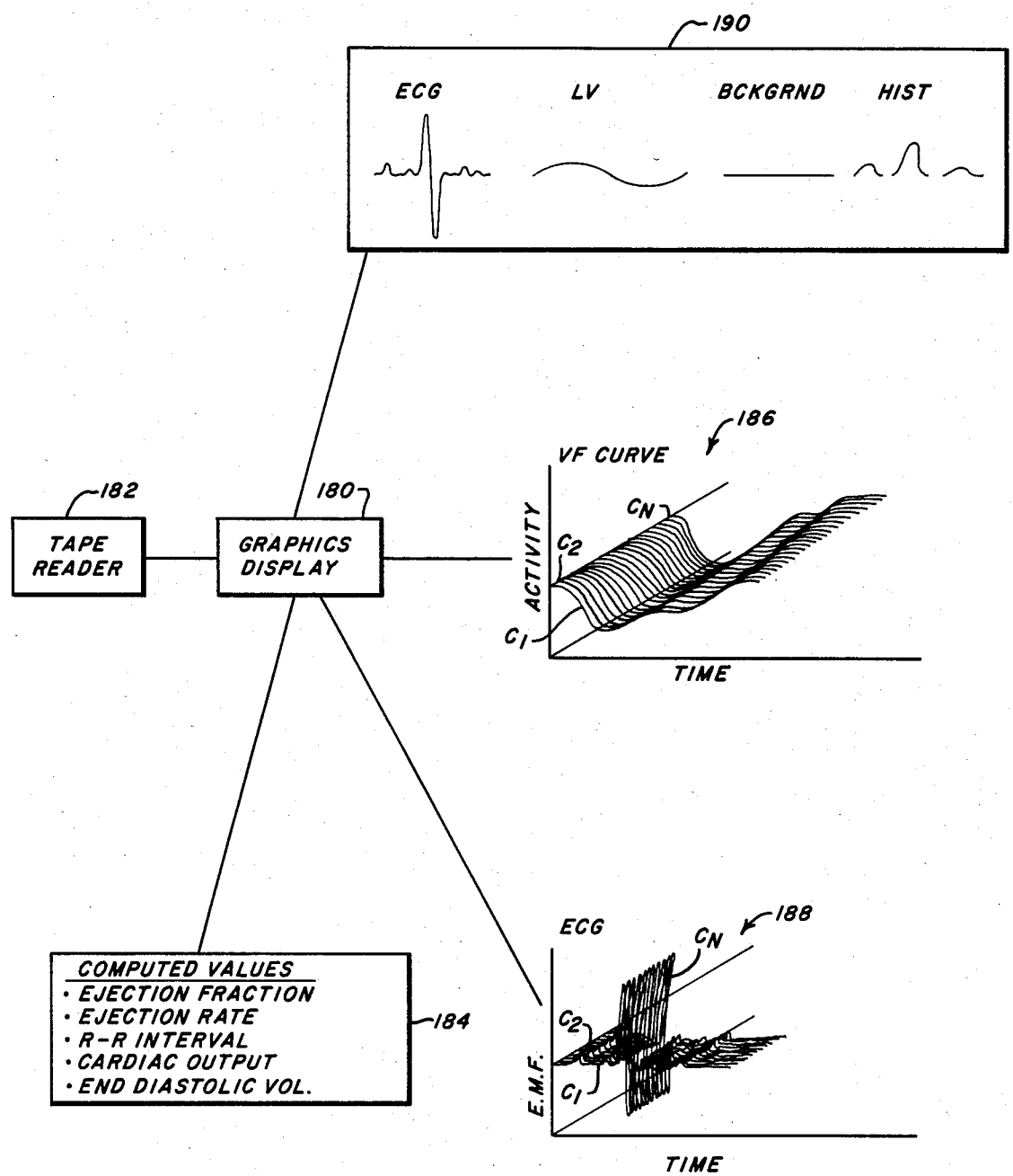
FIG. 8 is a diagram illustrating the graphics display system of the ventricular function monitor of the invention.

FIG. 8 designates at 180 the graphics display system of the ambulatory ventricular function monitor of the invention. The graphics display system 180, preferably an analog or digital computer-based display such as a Tektronix 4052 graphics terminal, is connected to a tape reader 182, preferably a VIP460, which reads the composite data in the plural categories representing PVC, NVC, and PPVC. The display is operative to compute such diagnostically useful parameters as the ejection fraction (EF), the ejection rate (ER), the R—R interval, the cardiac output, and the end diastolic activity as shown by the block 184.

The display 180 is also operative to display the data in a time-compressed isometric overlap mode. Graph 186 depicts an example of the operation in this mode for the nuclear ventricular time-activity and graph 188 depicts an example of the operation in this mode for the ECG activity. Both the time of occurrence and type of heart dysfunction can readily be identified over the duration of data collection from the graphs. Each curve represents an analog display of a recorded two or sixteen minute accumulation. The commencement point for the curves, labelled $C_1$ in both diagrams 186 and 188, is equal to the point $\tau_0(C_1) = X_o, Y_o$, where $X_o, Y_o = 0$. The commencement point for the $C_2$ curves is equal to the prior point plus a change in the X coordinate and a change in the Y coordinate, i.e., $\tau(C_2) = X_o + \Delta X, Y_o + \Delta Y$, and generally, $\tau(C_N) = X_{N-1} + \Delta X, Y_{N-1} + \Delta Y$. It will be appreciated that this ensembled display permits the presentation of the data over a long time interval and the quick identification of a point of anomalous behavior of cardiac dysfunction.

Once a point of cardiac dysfunction is identified, the graphics display 180 is used in a conventional manner to display the anomalous data as individual traces as shown in block 190. In this manner, the display can, for example, show a suitably trained specialist the particular ECG activity, the left ventricular time-activity, the background time-activity, and the R—R histogram for the particular point in time corresponding to the cardiac dysfunction.

It is to be understood that many modifications of the presently disclosed invention may be effected within the scope of the appended claims.

What is claimed is:

1. An ambulatory ventricular function recorder, comprising:
   a vest garment including means for removably supporting it about the human body;
   nuclear radiation detection first means, connected to and wholly supported in a body ambulatory manner by said garment, and adapted to respond to nuclear radiation from the region of the ventricle for repetitively providing an analog signal the amplitude of which cyclically represents the nuclear ventricular time-activity of the heart;
   second means, wholly suported in a body ambulatory manner by said garment and responsive to said analog signal, for repetitively providing a digital representation of said analog signal;
   third means, wholly supported in a body ambulatory manner by said garment and responsive to said digital representation, for accumulating said digital representation in storage so as to repetitively provide composite data that represents an average of said repetitively provided digital representation over successive time intervals that each correspond to a predetermined plurality of heart beats; and
   said third means including means for accumulating said digital representation in categories corresponding to premature, normal and post-premature ventricular contraction.

2. An ambulatory ventricular function recorder according to claim 1, wherein said removable supporting means of said garment includes means for removably supporting it about the torso of the human body.

3. An ambulatory ventricular function recorder according to claim 1, wherein said first means includes a main nuclear probe detector; and further including a separate background nuclear probe detector connected to said garment for providing a signal representing the nuclear time-activity of a preselected lung.

4. An ambulatory ventricular function recorder according to claim 3, wherein said main nuclear probe includes a housing having a mouth, a collimator positioned in said mouth, and a planar array of gamma photon radiation-sensitive crystals positioned in said housing and behind said collimator.

5. An ambulatory ventricular function recorder according to claim 4, wherein said housing and said collimator are made of lead, said lead collimator is provided with a plurality of parallel holes therethrough, and said crystals are CdTe radiation-sensitive detectors.

6. An ambulatory ventricular function recorder according to claim 4, further including a summer discriminator amplifier including a comparator having a preselected threshold responsive to the output signals of said radiation-sensitive crystals and operative to sum those output signals that exceed said preselected threshold to provide said analog signal.

7. An ambulatory ventricular function monitor according to claim 1, wherein said second means includes an analog-to-digital converter responsive to said analog signal and operative to provide a first digital pulse stream the frequency of which depends upon the magnitude of said analog signal, and said third means includes a microprocessor and associated memories responsive to said first digital pulse stream and operative to provide said data averaged over a plurality of cardiac cycles.

8. An ambulatory ventricular function monitor according to claim 7, wherein said microprocessor is operative for successive data collection intervals of said averaging time interval to sample said first pulse stream, to count the number of pulses which occur during respective sampling intervals of each data collection interval, and to accumulate the counts for successive sampling intervals in memory the address location of which depends on the phase of the particular sampling interval relative to the data collection interval.

9. An ambulatory ventriclar function monitor according to claim 8, further including fourth means coupled to said third means for separating said averaged data in plural categories representing PVC, NVC, and PPVC.

10. An ambulatory ventricular function monitor according to claim 9, wherein said fourth means includes separately addressable accumulating registers respectively dedicated to PVC, NVC, and PPVC.

11. An ambulatory ventricular function monitor according to claim 10, wherein said fourth means further include means for providing an electrocardiographic analog signal, an analog-to-digital converter responsive to said electrocardiographic analog signal and operative to provide a second digital pulse stream the frequency of which depends upon the magnitude of said analog electrocardiographic signal, and wherein said microprocessor is responsive to said first and said second digital pulse streams and operative to provide said averaged data in said separately addressable accumulating registers respectively dedicated to PVC, NVC, and PPVC.

12. An ambulatory ventricular function monitor according to claim 11, wherein said averaging time interval is two minutes.

13. An ambulatory ventricular function monitor according to claim 11, wherein said averaging time interval is sixteen minutes.

14. An ambulatory ventricular function monitor according to claim 1 or 11, further including a programmable oscilloscope operative to read and display said data and calculate and display selected cardiac ventricular parameters.

15. An ambulatory ventricular function monitor according to claim 1, wherein said third means includes a magnetic tape.

16. An ambulatory ventricular function monitor according to claim 1, wherein said third means includes a tiny disc.

17. An ambulatory ventricular function monitor according to claim 1, whereinsaid third means includes a bubble memory device.

18. A small, lightweight, and rugged nuclear probe detector assembly and ambulatory ventricular function monitor responsive thereto, comprising:
a vest garment including means for removably supporting it about the human body;
nuclear radiation detection first means, connected to and wholly supported in a body ambulatory manner by said garment, and adapted to respond to nuclear radiation from the region of the ventricle for repetitively providing an analog signal the amplitude of which cyclically represents the nuclear ventricular time-activity of the heart;
second means, wholly supported in a body ambulatory manner by said garment and responsive to said analog signal, for repetitively providing a digital representation of said analog signal;
third means, wholly supported in a body ambulatory manner by said garment and responsive to said digital representation, for accumulating said digital representation in storage so as to repetitively provide composite data that represents an average of said repetitively provided digital representation over successive time intervals that each correspond to a predetermined plurality of heartbeats;
said third means including means for accumulating said digital representation in categories corresponding to premature, normal and post-premature ventricular contraction;
said nuclear radiation detection first means including;
a radiation shield defining an enclosure having a mouth;
a plurality of gamma photon radiation-sensitive detectors arranged in a plane and mounted in said enclosure interiorly of said mouth; and
a collimator provided with an aperture pattern mounted to said mouth of said radiation shield extends over all of said plurality of gamma photon radiation-sensitive detectors.

19. A small, lightweight, and rugged nuclear probe detector assembly according to claim 18, wherein said collimator and said shield are made of lead.

20. A small, lightweight, and rugged nuclear probe detector assembly according to claim 19, wherein said lead collimator pattern includes a plurality of parallel hole apertures.

21. A small, lightweight, and rugged nuclear probe detector assembly according to claim 18, wherein said gamma photon radiation-sensitive detectors are CdTe crystals.

22. A small, lightweight, and rugged nuclear probe detector assembly according to claim 18, wherein said gamma photon radiation-sensitive detectors are germanium.

23. A small, lightweight, and rugged nuclear probe detector assembly according to claim 18, wherein said gamma photon radiation-sensitive detectors are sodium iodide crystals having an avalanche photodiode readout.

24. A small, lightweight, and rugged nuclear probe detector assembly according to claim 18, wherein said gamma photon radiation-sensitive detectors are plastic scintillation detectors having an avalanche photodiode readout.

25. A small, lightweight, and rugged nuclear probe detector assembly according to claim 18, wherein said gamma photon radiation-sensitive detectors are mercury cadmium telluride crystals.

26. A small, lightweight, and rugged nuclear probe detector assembly according to claim 18, wherein said gamma photon radiation-sensitive detectors are bismuth germanate crystals having an avalanche photodiode readout.

* * * * *

UNITED STATES PATENT AND TRADEMARK OFFICE
CERTIFICATE OF CORRECTION

PATENT NO.   : 4,633,881                      Page 1 of 2
DATED        : January 6, 1987
INVENTOR(S)  : Richard H. Moore; William Strauss; Nathaniel M. Alpert It is certified that error appears in the above—identified patent and that said Letters Patent is hereby corrected as shown below:

In the Abstract:

1st line  - "anaylzer" should read --analyzer--
   14th line - "sotred" should read --stored--

Column 1, line 6,    "HL 246623" should read --HL 24623--

Column 2, line 37,   "instrument of" should read --instrument system of--
          line 47,   "FIG. 4." should read --FIG. 4;--

Column 3, lines 31-32  "infor-   should read  --infor-
                        matiion"                mation--

Column 5, line 5,    "few" should read --fewer--
          line 15,   "on electrical" should read --an electrical--
          line 28,   "heat" should read --heart--
          line 29,   "heat" should read --heart--
          line 39,   "types" should read --type--

UNITED STATES PATENT AND TRADEMARK OFFICE
CERTIFICATE OF CORRECTION

PATENT NO. : 4,633,881

DATED : January 6, 1987

INVENTOR(S) : Richard H. Moore; William Strauss; Nathaniel M. Alpert

It is certified that error appears in the above-identified patent and that said Letters Patent is hereby corrected as shown below:

Column 7, line 60, "sixteen averaging" should read --sixteen minute averaging--

Column 10, line 19, "whereinsaid" should read --wherein said--

Signed and Sealed this

Twelfth Day of April, 1988

*Attest:*

DONALD J. QUIGG

*Attesting Officer*   *Commissioner of Patents and Trademarks*